(12) United States Patent
Brukilacchio

(10) Patent No.: US 8,629,982 B2
(45) Date of Patent: Jan. 14, 2014

(54) LIGHT EMITTING DIODE ILLUMINATION SYSTEM

(71) Applicant: Lumencor, Inc., Beaverton, OR (US)

(72) Inventor: Thomas J. Brukilacchio, Reading, MA (US)

(73) Assignee: Lumencor, Inc., Beaverton, OR (US)

( * ) Notice: Subject to any disclaimer, the term of this patent is extended or adjusted under 35 U.S.C. 154(b) by 0 days.

(21) Appl. No.: 13/968,178

(22) Filed: Aug. 15, 2013

(65) Prior Publication Data

US 2013/0334440 A1    Dec. 19, 2013

Related U.S. Application Data

(63) Continuation of application No. 13/344,815, filed on Jan. 6, 2012, now Pat. No. 8,525,999, which is a continuation of application No. 12/186,475, filed on Aug. 5, 2008, now Pat. No. 8,098,375.

(60) Provisional application No. 60/954,140, filed on Aug. 6, 2007.

(51) Int. Cl.
*G01N 21/00* (2006.01)

(52) U.S. Cl.
USPC .......................................... 356/432; 356/440

(58) Field of Classification Search
USPC .......... 356/239.2, 239.4, 239.6, 240.1, 241.1, 356/241.3, 241.5, 241.6, 402–420, 432, 356/43–50, 440; 362/227–228, 216–225, 362/217.01–217.17, 253–254, 260, 362/307–310, 257, 296.01, 317, 326–329, 362/23–30
See application file for complete search history.

(56) References Cited

U.S. PATENT DOCUMENTS

| | | | |
|---|---|---|---|
| 1,998,054 | A | 4/1935 | McBurney |
| 3,313,337 | A | 4/1967 | Bernat |
| 3,637,285 | A | 1/1972 | Stewart |
| 3,759,604 | A | 9/1973 | Thelen |
| 3,881,800 | A | 5/1975 | Friesem |
| 3,982,151 | A | 9/1976 | Ludovici |
| 4,003,080 | A | 1/1977 | Maiman |
| 4,298,820 | A | 11/1981 | Bongers |
| 4,371,897 | A | 2/1983 | Kramer |

(Continued)

FOREIGN PATENT DOCUMENTS

| | | |
|---|---|---|
| CA | 2 280 398 | 4/2000 |
| EP | 1 426 807 | 12/2003 |

(Continued)

OTHER PUBLICATIONS

International Search Report dated Sep. 4, 2013 for Application No. .PCT/US2013/043134, 11 pages.

(Continued)

*Primary Examiner* — Tri T Ton
(74) *Attorney, Agent, or Firm* — Fliesler Meyer LLP

(57) ABSTRACT

In various embodiments of the invention, a unique construction for Light Emitting Diodes (LEDs) with at least one luminescent rod and extracting optical elements used to generate a variety of high brightness light sources with different emission spectra. In an embodiment of the invention, forced air cooling is used to cool the luminescent rod. In an embodiment of the invention, totally internal reflected light can be redirected outward and refocused. In another embodiment of the invention, light emitted by the luminescent rod is outcoupled for use in a variety of applications.

27 Claims, 7 Drawing Sheets

(56) References Cited

U.S. PATENT DOCUMENTS

| | | |
|---|---|---|
| 4,510,555 A | 4/1985 | Mori |
| 4,539,687 A | 9/1985 | Gordon |
| 4,602,281 A | 7/1986 | Nagasaki et al. |
| 4,626,068 A | 12/1986 | Caldwell |
| 4,642,695 A | 2/1987 | Iwasaki |
| 4,644,141 A | 2/1987 | Hagen |
| 4,657,013 A | 4/1987 | Hoerenz et al. |
| 4,695,332 A | 9/1987 | Gordon |
| 4,695,732 A | 9/1987 | Ward |
| 4,695,762 A | 9/1987 | Bertstresser |
| 4,713,577 A | 12/1987 | Gualtieri |
| 4,724,356 A | 2/1988 | Daehler |
| 4,798,994 A | 1/1989 | Rijpers |
| 4,804,850 A | 2/1989 | Norrish et al. |
| 4,852,985 A | 8/1989 | Fujihara et al. |
| 4,937,661 A | 6/1990 | Van Der Voort |
| 4,995,043 A | 2/1991 | Kuwata |
| 5,052,016 A | 9/1991 | Mahbobzadeh |
| 5,089,860 A | 2/1992 | Deppe |
| 5,109,463 A | 4/1992 | Lee |
| 5,126,626 A | 6/1992 | Iwasaki |
| 5,128,846 A | 7/1992 | Mills et al. |
| 5,137,598 A | 8/1992 | Thomas |
| 5,193,015 A | 3/1993 | Shanks |
| 5,200,861 A | 4/1993 | Moskovich |
| 5,226,053 A | 7/1993 | Cho |
| 5,231,533 A | 7/1993 | Gonokami |
| 5,233,372 A | 8/1993 | Matsumoto |
| 5,249,195 A | 9/1993 | Feldman |
| 5,285,131 A | 2/1994 | Muller |
| 5,289,018 A | 2/1994 | Okuda |
| 5,312,535 A | 5/1994 | Waska |
| 5,315,128 A | 5/1994 | Hunt |
| 5,332,892 A | 7/1994 | Li et al. |
| 5,345,333 A | 9/1994 | Greenberg |
| 5,363,398 A | 11/1994 | Glass |
| 5,416,342 A | 5/1995 | Edmond et al. |
| 5,416,617 A | 5/1995 | Loiseaux |
| 5,418,584 A | 5/1995 | Larson |
| 5,428,476 A | 6/1995 | Jensen |
| 5,469,018 A | 11/1995 | Jacobsen |
| 5,475,281 A | 12/1995 | Heijboer |
| 5,478,658 A | 12/1995 | Dodabalapur |
| 5,489,771 A | 2/1996 | Beach et al. |
| 5,493,177 A | 2/1996 | Muller |
| 5,500,569 A | 3/1996 | Blomberg |
| 5,542,016 A | 7/1996 | Kaschke |
| 5,616,986 A | 4/1997 | Jacobsen |
| 5,644,676 A | 7/1997 | Blomberg |
| 5,658,976 A | 8/1997 | Carpenter |
| 5,669,692 A | 9/1997 | Thorgersen |
| 5,671,050 A | 9/1997 | De Groot |
| 5,674,698 A | 10/1997 | Zarling |
| 5,690,417 A | 11/1997 | Polidor et al. |
| 5,715,083 A | 2/1998 | Takayama |
| 5,719,391 A | 2/1998 | Kain |
| 5,757,014 A | 5/1998 | Bruno |
| 5,781,338 A | 7/1998 | Kapitza et al. |
| 5,803,579 A | 9/1998 | Turnbull et al. |
| 5,804,919 A | 9/1998 | Jacobsen |
| 5,808,759 A | 9/1998 | Okamori et al. |
| 5,827,438 A | 10/1998 | Blomberg |
| 5,833,827 A | 11/1998 | Anazawa |
| 5,858,562 A | 1/1999 | Utsugi |
| 5,864,426 A | 1/1999 | Songer |
| 5,942,319 A | 8/1999 | Oyama |
| 5,955,839 A | 9/1999 | Jaffe |
| 5,984,861 A | 11/1999 | Crowley |
| 6,110,106 A | 8/2000 | MacKinnon et al. |
| 6,154,282 A | 11/2000 | Lilge et al. |
| 6,198,211 B1 | 3/2001 | Jaffe |
| 6,204,971 B1 | 3/2001 | Morris |
| 6,222,673 B1 | 4/2001 | Austin |
| 6,293,911 B1 | 9/2001 | Imaizumi et al. |
| 6,299,338 B1 | 10/2001 | Levinson |
| 6,304,584 B1 | 10/2001 | Krupke |
| 6,366,383 B1 | 4/2002 | Roeder |
| 6,392,341 B2 | 5/2002 | Jacobsen |
| 6,404,127 B2 | 6/2002 | Jacobsen |
| 6,404,495 B1 | 6/2002 | Melman |
| 6,422,994 B1 | 7/2002 | Kaneko et al. |
| 6,444,476 B1 | 9/2002 | Morgan |
| 6,513,962 B1 | 2/2003 | Mayshack et al. |
| 6,517,213 B1 | 2/2003 | Fujita et al. |
| 6,529,322 B1 | 3/2003 | Jones |
| 6,542,231 B1 | 4/2003 | Garrett |
| 6,544,734 B1 | 4/2003 | Briscoe |
| 6,594,075 B1 | 7/2003 | Kanao et al. |
| 6,608,332 B2 | 8/2003 | Shimizu |
| 6,614,161 B1 | 9/2003 | Jacobsen |
| 6,614,179 B1 | 9/2003 | Shimizu et al. |
| 6,637,905 B1 | 10/2003 | Ng |
| 6,642,652 B2 | 11/2003 | Collins |
| 6,649,432 B1 | 11/2003 | Eilers |
| 6,674,575 B1 | 1/2004 | Tandler et al. |
| 6,680,569 B2 | 1/2004 | Mueller-Mach et al. |
| 6,685,341 B2 | 2/2004 | Ouderkirk et al. |
| 6,690,467 B1 | 2/2004 | Reel |
| 6,717,353 B1 | 4/2004 | Mueller |
| 6,747,710 B2 | 6/2004 | Hall |
| 6,791,259 B1 | 9/2004 | Stokes et al. |
| 6,791,629 B2 | 9/2004 | Moskovich |
| 6,795,239 B2 | 9/2004 | Tandler et al. |
| 6,843,590 B2 | 1/2005 | Jones |
| 6,869,206 B2 | 3/2005 | Zimmerman et al. |
| 6,870,165 B2 | 3/2005 | Amirkhanian |
| 6,926,848 B2 | 8/2005 | Le Mercier |
| 6,958,245 B2 | 10/2005 | Seul et al. |
| 6,960,872 B2 | 11/2005 | Beeson et al. |
| 6,981,970 B2 | 1/2006 | Karni |
| 6,991,358 B2 | 1/2006 | Kokogawa |
| 6,995,355 B2 | 2/2006 | Rains, Jr. et al. |
| 7,009,211 B2 | 3/2006 | Eilers |
| 7,011,421 B2 | 3/2006 | Hulse et al. |
| 7,035,017 B2 | 4/2006 | Tadic-Galeb |
| 7,083,610 B1 | 8/2006 | Murray et al. |
| 7,141,801 B2 | 11/2006 | Goodwin |
| 7,153,015 B2 | 12/2006 | Brukilacchio |
| 7,192,161 B1 | 3/2007 | Cleaver et al. |
| 7,205,048 B2 | 4/2007 | Naasani |
| 7,208,007 B2 | 4/2007 | Nightingale et al. |
| 7,211,833 B2 | 5/2007 | Slater, Jr. et al. |
| 7,239,449 B2 | 7/2007 | Leitel et al. |
| 7,300,175 B2 | 11/2007 | Brukilacchio |
| 7,316,497 B2 | 1/2008 | Rutherford et al. |
| 7,384,797 B1 | 6/2008 | Blair |
| 7,416,313 B2 | 8/2008 | Westphal et al. |
| 7,422,356 B2 | 9/2008 | Hama et al. |
| 7,427,146 B2 | 9/2008 | Conner |
| 7,445,340 B2 | 11/2008 | Conner |
| 7,467,885 B2 | 12/2008 | Grotsch et al. |
| 7,488,088 B2 | 2/2009 | Brukilacchio |
| 7,488,101 B2 | 2/2009 | Brukilacchio |
| 7,498,734 B2 | 3/2009 | Suehiro et al. |
| 7,540,616 B2 | 6/2009 | Conner |
| 7,595,513 B2 | 9/2009 | Plank et al. |
| 7,633,093 B2 | 12/2009 | Blonder et al. |
| 7,709,811 B2 | 5/2010 | Conner |
| 7,746,560 B2 | 6/2010 | Yamazaki |
| 7,832,878 B2 | 11/2010 | Brukilacchio |
| 7,837,348 B2 | 11/2010 | Narendran et al. |
| 7,846,391 B2 | 12/2010 | Jaffe et al. |
| 7,854,514 B2 | 12/2010 | Conner |
| 7,857,457 B2 | 12/2010 | Rutherford et al. |
| 7,898,665 B2 | 3/2011 | Brukilacchio et al. |
| 7,976,307 B2 | 7/2011 | Plank et al. |
| 8,029,142 B2 | 10/2011 | Conner |
| 8,098,375 B2 | 1/2012 | Brukilacchio |
| 8,242,462 B2 | 8/2012 | Jaffe et al. |
| 8,258,487 B1 | 9/2012 | Jaffe et al. |
| 8,263,949 B2 | 9/2012 | Jaffe et al. |
| 8,279,442 B2 | 10/2012 | Brukilacchio et al. |
| 8,309,940 B2 | 11/2012 | Jaffe et al. |
| 8,389,957 B2 | 3/2013 | Jaffe et al. |

(56) References Cited

U.S. PATENT DOCUMENTS

| | | |
|---|---|---|
| 8,466,436 B2 | 6/2013 | Jaffe et al. |
| 8,493,564 B2 | 7/2013 | Brukilacchio et al. |
| 2001/0055208 A1 | 12/2001 | Kimura |
| 2002/0109844 A1 | 8/2002 | Christel et al. |
| 2002/0127224 A1 | 9/2002 | Chen |
| 2003/0044160 A1 | 3/2003 | Jones et al. |
| 2003/0095401 A1 | 5/2003 | Hanson et al. |
| 2003/0127609 A1 | 7/2003 | El-Hage et al. |
| 2003/0160151 A1 | 8/2003 | Zarate et al. |
| 2003/0230728 A1 | 12/2003 | Dai |
| 2003/0233138 A1 | 12/2003 | Spooner |
| 2004/0090600 A1 | 5/2004 | Blei |
| 2004/0090794 A1 | 5/2004 | Ollett et al. |
| 2004/0247861 A1 | 12/2004 | Naasani |
| 2004/0264185 A1 | 12/2004 | Grotsch et al. |
| 2005/0062404 A1 | 3/2005 | Jones et al. |
| 2005/0116635 A1 | 6/2005 | Walson et al. |
| 2005/0146652 A1 | 7/2005 | Yokoyama et al. |
| 2005/0152029 A1 | 7/2005 | Endo |
| 2005/0184651 A1 | 8/2005 | Cheng |
| 2005/0201899 A1 | 9/2005 | Weisbuch |
| 2005/0248839 A1 | 11/2005 | Yamaguchi |
| 2005/0260676 A1 | 11/2005 | Chandler |
| 2005/0263679 A1 | 12/2005 | Fan |
| 2006/0002131 A1 | 1/2006 | Schultz et al. |
| 2006/0030026 A1 | 2/2006 | Garcia |
| 2006/0060872 A1 | 3/2006 | Edmond et al. |
| 2006/0060879 A1 | 3/2006 | Edmond |
| 2006/0114960 A1 | 6/2006 | Snee |
| 2006/0170931 A1 | 8/2006 | Guo |
| 2006/0237658 A1 | 10/2006 | Waluszko |
| 2006/0282137 A1 | 12/2006 | Nightingale et al. |
| 2007/0053184 A1 | 3/2007 | Brukilacchio |
| 2007/0053200 A1 | 3/2007 | Brukilacchio |
| 2007/0058389 A1 | 3/2007 | Brukilacchio |
| 2007/0064202 A1 | 3/2007 | Moffat et al. |
| 2007/0086006 A1 | 4/2007 | Ebersole et al. |
| 2007/0126017 A1 | 6/2007 | Krames et al. |
| 2007/0211460 A1 | 9/2007 | Ravkin |
| 2007/0253733 A1 | 11/2007 | Fey |
| 2007/0262731 A1 | 11/2007 | Jaffar et al. |
| 2007/0279914 A1 | 12/2007 | Rutherford et al. |
| 2007/0279915 A1 | 12/2007 | Rutherford et al. |
| 2007/0280622 A1 | 12/2007 | Rutherford |
| 2007/0281322 A1 | 12/2007 | Jaffe et al. |
| 2007/0284513 A1 | 12/2007 | Fan et al. |
| 2007/0297049 A1 | 12/2007 | Schadwinkel et al. |
| 2008/0079910 A1 | 4/2008 | Rutherford et al. |
| 2008/0224024 A1 | 9/2008 | Ashdown |
| 2008/0291446 A1 | 11/2008 | Smith |
| 2009/0122533 A1 | 5/2009 | Brukilacchio |
| 2009/0196046 A1 | 8/2009 | Rutherford et al. |
| 2009/0268461 A1 | 10/2009 | Deak et al. |
| 2010/0188017 A1 | 7/2010 | Brukilacchio |
| 2011/0044858 A1 | 2/2011 | Jaffe et al. |
| 2012/0106192 A1 | 5/2012 | Brukilacchio |
| 2012/0181936 A1 | 7/2012 | Jaffe et al. |
| 2012/0181937 A1 | 7/2012 | Jaffe et al. |
| 2012/0238472 A1 | 9/2012 | Jaffe et al. |
| 2012/0252704 A1 | 10/2012 | Jaffe et al. |
| 2012/0307514 A1 | 12/2012 | Brukilacchio et al. |
| 2013/0099135 A1 | 4/2013 | Jaffe et al. |
| 2013/0188331 A1 | 7/2013 | Jaffe et al. |
| 2013/0188383 A1 | 7/2013 | Jaffe et al. |
| 2013/0188384 A1 | 7/2013 | Jaffe et al. |
| 2013/0188388 A1 | 7/2013 | Jaffe et al. |

FOREIGN PATENT DOCUMENTS

| | | |
|---|---|---|
| GB | 0943756 | 12/1963 |
| GB | 2 000 173 A | 1/1979 |
| JP | 2005-195485 | 7/2005 |
| JP | 2005-243973 | 9/2005 |
| JP | 2006-049814 | 2/2006 |
| JP | 2007-133435 | 5/2007 |
| KR | 10-2006-0055934 | 5/2006 |
| WO | WO 02/080577 | 10/2002 |
| WO | WO 2004/114053 | 12/2004 |
| WO | WO 2006/067885 | 6/2006 |
| WO | WO 2006/120586 | 11/2006 |

OTHER PUBLICATIONS

International Search Report dated Dec. 31, 2008, Application No. PCT/US2008/072394, 10 pages.

International Search Report for PCT/US2010021843 dated Aug. 19, 2010, 9 pages.

Extended European Search Report for PCT/US2008072394 dated Oct. 7, 2011, 9 pages.

International Search Report dated Jun. 19, 2012 for Application No. PCT/US2011/063030, 11 pages.

Extended European Search Report for PCT/US2007/069490 dated Oct. 26, 2012, 8 pages.

International Search Report dated Jun. 3, 2013 for Application No. PCT/US2013/029931, 11 pages.

Albrecht, M., et al., "Scintillators and Wavelength Shifters for the Detection of Ionizing Radiation," Astroparticle, Particle and Space Physics, Detectors and Medical Physics Applications, ICATPP-8, M. Barone, et al., Eds, World Scientific, pp. 502-511 (2004).

Da-Lite Screen Company, Inc., www.da-lite.com, 46 pages website downloads as of Oct. 8, 1998.

DDS™ Rear Projection Screens, LORS™ Reflection Screens, © 1998 Physical Optics Corporation, Torrance, CA, 2 pages.

Deck, L., et al., "Two color light-emitting-diode source for high precision phase-shifting interferometry", Optics Letters, vol. 18, No. 22, Nov. 15, 1993, pp. 1899-1901.

Depp, S.W., et al., "Flat Panel Displays," Scientific American, pp. 90-97, Mar. 1993.

Flor-Henry, M., et al., "Use of a Highly Sensitive Two-Dimensional Luminescence Imaging System to Monitor Endogenous Bioluminescence in Plant Leaves," BMC Plant Biology, vol. 4, No. 19, Nov. 2004.

Hamberg, I. and Granqvist, C.G., "Evaporated Sn-doped $In_2O_3$ films: Basic optical properties and applications to energy-efficient windows," Journal of Applied Physics, vol. 60, No. 11, pp. R123-R159, Dec. 1, 1986.

Handbook of Optics, vol. 1—Fundamentals, Techniques, and Design, Second Edition, Chapter 42: Optical Properties of Films and Coatings, J.A. Dobrowolski, pp. 42.3-42.25, McGraw-Hill, Inc., © 1995.

Haroche, S., et al., "Cavity Quantum Electrodynamics," Scientific American, pp. 54-62, Apr. 1993.

Hecht, Jeff, "Diverse fiberoptic systems require varied sources," Laser Focus World, vol. 36, No. 1, pp. 155-161, Jan. 2000.

Hemingway, D.J. and Lissberger, P.H., "Effective Refractive Indices of Metal-Dielectric Interference Filters," Applied Optics, vol. 6, No. 3, pp. 471-476, Mar. 1967.

Hinds, E.A., "Spectroscopy of Atoms in a Micron-Sized Cavity," (date and periodical title unknown), pp. 18-19.

Holloway, R.J. and Lissberger, P.H., "The Design and Preparation of Induced Transmission Filters," Applied Optics, vol. 8, No. 3, pp. 653-660, Mar. 1969.

Huo, D.T.C., et al., "Reticulated Single-Crystal Luminescent Screen," J. Electrochem. Soc., vol. 133, No. 7, pp. 1492-1497, Jul. 1986.

Jenmar Visual Systems, Sunnyvale, CA, 4 pages, no date, but at least as early as Oct. 15, 1998.

Landau, B.V. and Lissberger, P.H., "Theory of Induced-Transmission Filters in Terms of the Concept of Equivalent Layers," Journal of the Optical Society of America, vol. 62, No. 11, pp. 1258-1264, Nov. 1972.

Launer, Herbert F., "Exposure Meter for Precision Light Dosage", The Review of Scientific Instruments, vol. 20, No. 2, Feb. 1949, pp. 103-109.

Lissberger, P.H., "Coatings with Induced Transmission," Applied Optics, vol. 20, No. 1, pp. 95-103, Jan. 1, 1981.

(56) References Cited

OTHER PUBLICATIONS

Mauch, R.H., et al., "Optical Behaviour of Electroluminescent Devices," Springer Proceedings in Physics, vol. 38, Electroluminescence, © Springer-Verlag Berlin, Heidelberg, pp. 291-295 (1989).

Morgan, C. G., et al., "New Approaches to Lifetime-Resolved Luminescence Imaging", Journal of Fluorescence, vol. 7, No. 1, 1997, pp. 65-73.

Pelletier, E. and MacLeod, H.A., "Interference Filters with Multiple Peaks," Journal of the Optical Society of America, vol. 72, No. 6, pp. 683-687, Jun. 1982.

Plasma Display Manufacturers of the American Display Consortium, "Recommended Research Topics on Plasma Display for the DARPA Sponsored Phosphor Center of Excellence," pp. 1-2, Mar. 24, 1993.

Poelman, D., et al., "Spectral Shifts in Thin Film Electroluminescent Devices: An Interference Effect," J. Phys. D: Appl. Phys., vol. 25, pp. 101-1013 (1992).

Schott Glass Technologies, Inc., Schott Total Customer Care, Contrast Enhancement Filters, Duryea, PA, 6 pages, Jan. 1998.

Schubert, E.F., et al., "Giant Enhancement of Luminescence Intensity in Er-doped $Si/SiO_2$ Resonant Cavities," Appl. Phys. Lett. vol. 61, No. 12, pp. 1381-1383, Sep. 21, 1992.

Stewart Filmscreen Corporation®, www.stewartfilm.com, 34 pages website downloads as of Oct. 8, 1998.

Tuenge, R.T., "Current Status of Color TFEL Phosphors," Electroluminescence—Proceedings of the Sixth International Workshop on Electroluminescence, El Paso, Tex., pp. 173-177, May 1992.

Vlasenko, N.A., et al., "Interference of Luminescent Emission from an Evaporated Phosphor," Opt. Spect., vol. 11, pp. 216-219 (1961).

Vlasenko, N.A., et al., "Investigation of Interference Effects in Thin Electroluminescent ZnS-Mn Films," Opt. Spect., vol. 28, pp. 68-71 (1970).

Whitaker, Jerry C., "Electronic Displays: Technology, Design, and Applications," McGraw-Hill, Inc., pp. 185-192 (1994).

World Watch, Photonics Spectra, "IR Reflective Coating Boosts Bulb's Output, Recycling of IR Energy Saves Power, Cuts Costs" pp. 40-41, Jan. 1991.

Yamamoto, Y., et al., "Optical Processes in Microcavities," Physics Today, pp. 66-73, Jun. 1993.

Yokoyama, H., "Physics and Device Applications of Optical Microcavities," Science, vol. 256, pp. 66-70, Apr. 3, 1992.

Young, L., "Multilayer Interference Filters with Narrow Stop Bands," Applied Optics, vol. 6, No. 2, pp. 297-312, Feb. 1967.

LIGHT EMITTING DIODE ILLUMINATION SYSTEM

PRIORITY CLAIM

This application is a continuation of U.S. patent application Ser. No. 13/344,815, filed Jan. 6, 2012, entitled "LIGHT EMITTING DIODE ILLUMINATION SYSTEM", which is a continuation of U.S. patent application Ser. No. 12/186,475, filed Aug. 5, 2008, (now U.S. Pat. No. 8,098,375), entitled "LIGHT EMITTING DIODE ILLUMINATION SYSTEM", which claims priority to U.S. Provisional Patent Application No: 60/954,140, entitled: "LIGHT EMITTING DIODE ILLUMINATION SYSTEM", filed Aug. 6, 2007, which applications are incorporated herein by reference in their entireties.

CROSS REFERENCE TO RELATED APPLICATIONS

This application is related to U.S. patent application Ser. No. 12/187,356 entitled "LIGHT EMITTING DIODE ILLUMINATION SYSTEM" filed Aug. 6, 2008 by Thomas Brukilacchio and Arlie Connor (now U.S. Pat. No. 7,898,665) which application is incorporated herein by reference in its entirety.

FIELD OF THE INVENTION

This invention, in general, relates to high brightness illumination sources and more particularly to the use of light emitting diodes (LEDs) as a source of illumination for medical endoscopy.

BACKGROUND OF THE INVENTION

There is a significant need for high brightness broad band illumination sources to provide optical fiber coupled illumination for surgical endoscopy and other applications where extremely high brightness sources are needed such as in projection systems and high speed industrial inspection. Prior art typically utilize short arc lamps such as high pressure mercury, metal halide, and xenon. These lamps are capable of very high luminous emittance and are therefore suitable sources for the etendue limited fiber optic coupled illumination systems. Approximately 85% of the high brightness illumination sources in use in the operating room today are based on compact short arc xenon lamps. The problems associated with these lamp technologies, however, include poor luminous efficacy thereby requiring high power and associated means of cooling, short lifetime, high voltage operation (typically kilovolts required to turn them on), high cost, and use of mercury which is becoming an environmental hazard and is in the process of undergoing regulations in numerous countries throughout the world.

Only recently has there been recognition that LEDs may provide sufficient illumination to be used to replace more traditional light sources in endoscopic illumination systems. In particular, LEDs provide much improved lifetime, lower cost of ownership, lower power consumption (enabling some battery operated portable devices), decreased cooling requirements, and freedom form mercury relative to conventional arc lamps. Additionally they can be readily modulated which can be a significant advantage in many applications. To date no LED based endoscopic illumination system commercially exists that equals or exceeds the luminous intensity of the compact xenon arc lamp systems. The invention described herein has the potential of meeting and exceeding the output of the best arc lamps systems available today

SUMMARY

The invention herein describes a white light illumination system which incorporates a luminescent rod material which is excited along its length by a linear array of LEDs. In a preferred embodiment the luminescent material is single crystal or sintered ceramic Ce:YAG (cerium doped yttrium aluminum gamete, $Y_3Al_5O_{12}:Ce^{3+}$) and the LEDs are blue GaN based surface emitting devices. The green and or yellow output spectrum from the rod is index matched to a collection optic which converts the light emitted from the aperture of the rod to a larger dimension with a smaller solid angle to allow it to be imaged to a fiber bundle. The output of the luminescent rod and collection optic could be combined with the output of other directly coupled LED arrays in the blue and green spectral regions to produce white light. While blue and red LED modules can be produced to equal or exceed the brightness of conventional high brightness light sources such as compact xenon arc lamps, the efficiency of LEDs in the true green spectrum in the spectral region of 555 nm are of comparatively low efficiency and are not sufficiently bright compared to arc lamps.

Typically light generated from LEDs in the spectral region of 555 nm is achieved by applying a thin layer of encapsulant with phosphor suspended in it directly over LED die emitting blue light. The light from the phosphor particles is partially absorbed and partially scattered. The combination of the scattered blue light and the absorbed light re-emitted as luminescent light at longer wavelengths typically in the green and red spectral region produces white light.

The amount of white light produced can be increased by increasing the current density to the LED up to the point where the output of the LED rolls over and no longer increases with increasing current. The brightness of any LED made by in this general configuration is fundamentally limited by the internal and external quantum efficiency of the LED die, the quantum efficiency of the luminescent material, the amount of scattering by the particles, the thermal quenching properties of the die, and the die junction temperature. In contrast, the present invention is not limited by the current density of the LED as the length of the rod material could be increased to increase the number of excitation LED die and thereby increasing the output. For example, a high performance LED die with a 1 mm square area coated with a high performance phosphor can produce approximately 200 Lumens with a heat sink temperature near room temperature before rolling over and no longer producing more light with further increases in current density.

A luminescent rod of the present invention with the same 1 mm square cross sectional area with a length of 50 mm could have on the order of 100 LEDs exciting the rod. As will be shown in the detailed description below, a conservative efficiency of 30% would result in an output of more than an order of magnitude higher photometric power with each LED operating at significantly lower current densities. Furthermore, if higher output was required the length of the rod could be increased along with an increase in the number of LEDs exciting the luminescent rod. Thus the present invention comprises a means of producing output in the green portion of the spectrum that is of higher brightness than can be achieved by even the best xenon short arc lamps.

BRIEF DESCRIPTION OF THE DRAWINGS

This invention is described with respect to specific embodiments thereof. Additional features can be appreciated from the Figures in which.

DETAILED DESCRIPTION OF THE INVENTION

Figure 1:
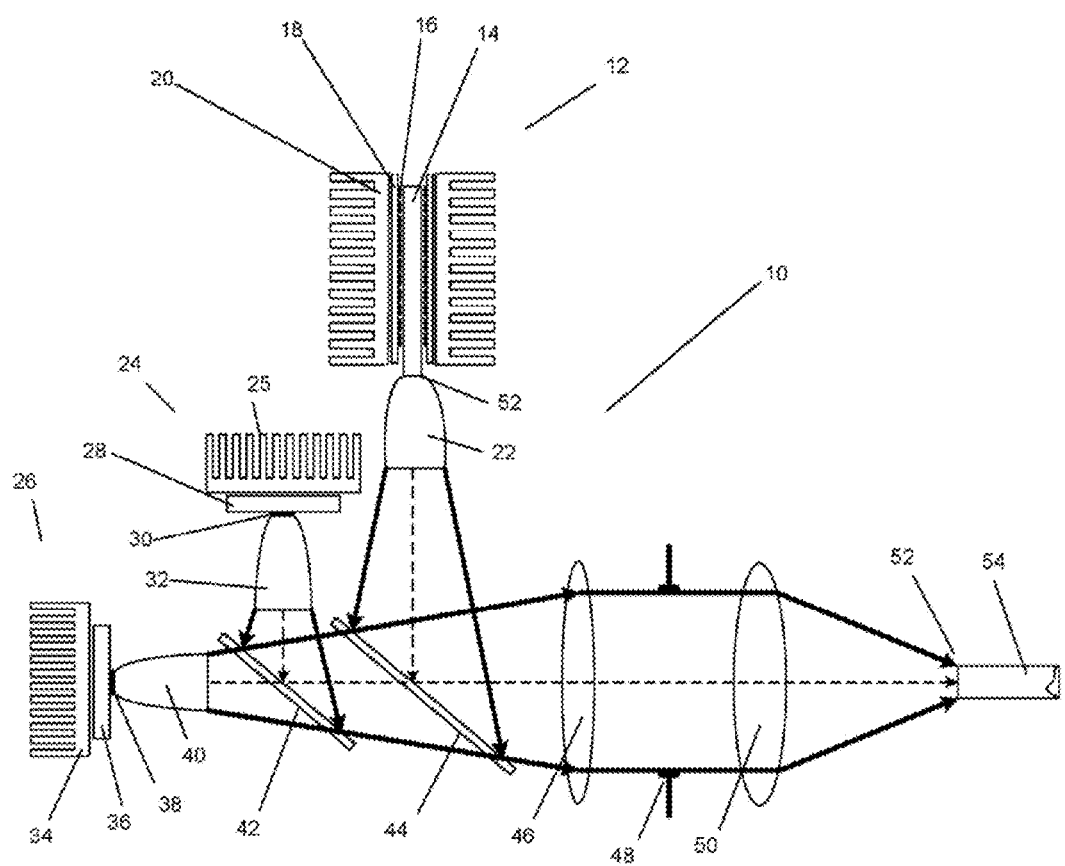
FIG. 1 shows a preferred embodiment of the light emitting diode illumination system. Three spectral coupled sources generally in the blue, green, and red portions of the spectrum are combined to provide a high brightness light source capable of providing illumination sufficient for fiber optic coupled endoscopic illumination medical endoscopy.

The present invention relates to high brightness fiber optic illumination systems. In particular, the present invention represents an LED based light source for improved illumination systems relative to arc lamp and other LED based light source systems. The illumination system 10 of FIG. 1 is comprised of one or more LED die or die array modules 12, 24 and 26 spectrally and spatially combined by means such as dichroic beam splitters 42 and 44 coupled to a common source aperture 52 which substantially conserves the etendue or area, solid angle, index squared product. A preferred embodiment of the system couples into an optical fiber bundle to provide the high luminous power and high brightness required for medical endoscopic applications. Other high brightness applications include, but are not limited to, projection systems, industrial illumination, photo curing, spot lights, and medical photodynamic therapy.

Prior to LED based systems conventional arc lamp based projection systems were used comprised of a short arc lamp typically of the high pressure mercury, metal halide, or xenon lamp variety. The primary disadvantage of the short arc technology is lamp life, which is typically in the 500 to 1000 hour range. The cost of the arc lamp itself and the service cost to replace the lamps over the life of the product can be many multiples of the original cost of the complete illumination system. This drive hospital costs up which in turn drive the costs of medical insurance up. Additional benefits of the LED technology include reduced power consumption, low voltage operation, light intensity stability, ability to control correlated color temperature (CCT) and color rendering index (CRI), and the ability to modulate the source. The ability to modulate the source can be a significant benefit. For example, most of the endoscopic systems in use today are coupled to a video camera. Typically video cameras incorporate an electronic shutter and typically the video signal is not integrated continuously. Thus, there is an opportunity to modulate the LED source in synchronization with the shutter. During the time when the shutter is closed, the LED light source does not need to be on. Thus, for example, if the shutter was open 50% of the time, the light source could be modulated in synchronization producing 50% less heat. Thus, for the same average input power to the LED light source the light output could be increased by an amount dependant on the operating point of the LED source with respect to efficiency.

A more conventional approach to producing white light by LEDs is to deposit a phosphor powder, typically of Ce:YAG (cerium doped yttrium aluminum garnet, $Y_3Al_5O_{12}:Ce^{3+}$) suspended in an encapsulant material such as silicone, onto a blue LED die or die array with a peak wavelength between about 445 nm and 475 nm. The light absorbed by the phosphor is converted to yellow light which combines with the scattered blue light to produce a spectrum that appears white. The apparent color temperature is a function of the density and thickness of the phosphor suspended in the encapsulant. While this approach is efficient, the amount of white light produced per unit area per unit solid angle is fundamentally limited by the amount of blue light extracted from the blue LED die or die array, the quantum efficiency of the phosphor, the phosphors thermal quenching, and the back scattering, which is a function of the particle size of the phosphor or other luminescent material. While it is feasible to place a solid phosphor such as single crystal Ce:YAG over the top of the blue LED die or die array, the change in effective path length with angle which increases from normal incidence as the rays approach the plane of the LED die emitting surface produces a change in spectrum with angle resulting in a non-uniform far field distribution and undesirable color variation. Furthermore, the efficiency of such a device would be limited by the total internal reflection of such a luminescent material due to its high index of refraction unless the surface was in contact with an index matching medium or included a structure to increase extracted radiance such as a photonic lattice, surface roughened or micro-lens array.

The heart of the invention of FIG. 1 is the LED source module 12 comprised of a central rod 14 of luminescent material such as single crystal or sintered ceramic Ce:YAG, and other luminescent materials including: $(Lu_{1-x-y-a-b}Y_xGd_y)_3(Al_{1-z-c}Ga_zSi_c)_5O_{12-c}N:Ce_aPr_b$ with $0<x<1$, $0<y<1$, $0<z</=0.1$, $0<a<=0.2$, $0<b<=0.1$, and $0<c<1$ for example $Lu_3Al_5O_{12}:Ce^{3+}$, $Y_3Al_5O_{12}:Ce^{3+}$ and $Y_3Al_{4.8}Si_{0.2}O_{11.8}N_{0.2}:Ce^{3+}$ emitting yellow-green light; and $(Sr_{1-x-y}Ba_xCa_y)_{2-z}Si_{5-a}Al_aN_{8-a}O_a:Eu_z^{2+}$ where $0<=a<5$, $0<x<=1$, $0<=y<=1$, and $0<z<=1$ for example $Sr_2Si_5N_8:Eu^{3+}$, emitting red light. Other candidates include $(Sr_{1-a-b}Ca_bBa_c)Si_xN_yO_z:Eu_a^{2+}$ where $a=0.002$ to $0.20$, $b=0.0$ to $0.25$, $c=0.0$ to $0.25$, $x=1.5$ to $2.5$, $y=1.5$ to $2.5$, and $z=1.5$ to $2.5$ for example $SrSi_2N_2O_2:Eu^{2+}$; $(Sr_{1-u-v-x}Mg_uCa_vBa_x)(Ga_{2-y-z}Al_zIn_zS_4):Eu^{2+}$ for example $SrGa_2S_4:Eu^{2+}$; $(Sr_{1-x-y}Ba_xCa_y)_2SiO_4:Eu^{2+}$ for example $SrBaSiO_4:Eu^{2+}$; $(Ca_{1-x}Sr_x)S:Eu^{2+}$ where $0<x<=1$ for example $CaS:Eu^{2+}$ and $SrS:Eu^{2+}$; $(Ca_{1-x-y-z}Sr_xBa_yMg_z)_{1-x}(Al_{1a+b}B)Si_{1-b}N_{3-b}O_b:RE_n$ where $0<=x<=1$, $0<=y<=1$, $0<=z<=1$, $0<=a<=1$, $0<=b<=1$ and $0.002<=n<=0.2$ and RE is either europium(II) or cerium(Ill) for example $CaAlSiN_3:Eu^{2+}$ or $CaAl_{1.04}Si_{0.96}N_3:Ce^{3+}$; and $M_xv+Si_{12-(m+n)}Al_{m+n}O_nN_{16-n}$ with $x=m/v$ and M comprised of a metal preferably selected from the group comprising Li, M, Ca, Y, Sc, Ce, Pr, Nd, Sm, Eu, Gd, Tb, Dy, Ho, Er, Tm, Yb, Lu or mixtures including for example $Ca_{0.75}Si_{8.625}Al_{3.375}N_{0.625}:Eu_{0.25}$ as disclosed in U.S. patent application Ser. No. 11/290,299 to Michael R. Krames and Peter J. Schmidt (publication #2007/0126017) which is herein explicitly incorporated by reference in its entirety; and nanophosphors embedded in a suitable matrix such as high index plastic or glass, with LED die positioned along its length in a linear array of die or a single long LED die attached to a high thermal conductivity board 18, such as copper or aluminum core printed circuit board, which in turn is attached to heat sink 20. The luminescent rod 14 would have the properties of high absorption of light in one part of the spectrum, blue in the case of Ce:YAG, emission with high quantum yield in a wavelength region generally longer than the excitation wavelength band, high index of refraction to trap a significant portion of the luminescent light produced such that it is guided or transmitted down the length of the rod toward an emitting aperture 52. The emitting aperture would be index matched to an optical concentrator 22 such as a compound parabolic concentrator (CPC), compound elliptical concentrator (CEC), compound hyperbolic concentrator (CHC), taper, or faceted optic. The concentrators would generally be index matched and of solid dielectric, although liquids could work as well. The purpose of the concentrator is two-fold. First, it would be made of a material with an index of refraction approaching that of the rod (approximately 1.82 for Ce:YAG) and second, it would act to convert the light emitted over a hemisphere ($2\pi$ steradians) to an area and solid angle that can be readily imaged through dichroic beam splitters and re-imaging optics while substantially preserving the etendue (area, solid angle, index squared product) thereby maximizing the brightness.

The output spectrum of the Ce:YAG rod source would cover the range between about 500 nm and 700 nm, with the predominant contribution in the green spectrum centered around 555 nm. The combination of this light with that from a blue LED module 24 would produce white light suitable for many applications. For medical illumination, however, the relative spectral content is typically required to result in a high color rendering index (CRI) on the order of 85 or greater. To accomplish this it is necessary to add additional light in the red spectral region from a third LED source module 26. In FIG. 1 dichroic beam splitter 42 would transmit the red light of LED module 26 and reflect the blue light of LED module 24. Dichroic beam splitter 44 would transmit the combined blue and red spectrum of combined LED modules 26 and 24 and reflect the green or yellow light of LED module 12. The combined white light spectrum from LED modules 12, 24, and 26 would then be imaged by lens elements 46 and 50 to stop the input aperture 52 of fiber optic light bundle 54. The lens elements 46 and 50 could be comprised of multiple lens elements which may include glasses or plastics of different dispersions to help optimize image quality. The lens systems stop 48 would assure that the extent of the far field of the light from each LED module was similar so as not to result in color fringe effects at the edge of the illumination field. The size of each LED source and their collection optics would be sized such as to produce substantially similar near and far field distributions for each LED module. The lens system could also include diffractive or reflective components to help reduce the number of or optical elements and to reduce overall package size. The relative position of the LED modules 12, 24, and 26 are interchangeable assuming that the dichroic beam splitters were changed in spectral characteristics to accommodate different arrangements. For example, LED modules 12 and 24 could be switched in position such that beam splitter 42 would transmit red light, reflect blue and green light and beam splitter 44 would transmit red and green and reflect blue light. The spectrum of the LED modules in a different system could include ultraviolet through mid infrared light assuming the optical elements where made of the proper transmitting materials and anti-reflection or reflection coatings. The LED modules 24 and 26 would be comprised of an LED array either index matched or not index matched to the collection optic depending on the extraction efficiency and method of the LED die. For example blue die form CREE (EZ1100) includes a micro lens array such that the benefit from index matching does not compensate for the increase in the etendue due to the index squared effect. Thus for the case of these high performance blue die higher brightness is achieved by not index matching. The red die that are commercially available at this time do not typically include microstructures on their surface to significantly enhance extraction efficiency and thus do benefit from encapsulation, not from a brightness standpoint, but from an efficiency standpoint which due to decreased thermal load translates into improved performance. The collection optics could be comprised of similar optics as detailed for the LED module 12, however, in the case of the blue die, the CPC, taper, or other concentrator could be designed for no index matching.

Heat sinks 12, 25, and 34 of FIG. 1 could be made out of any high thermal conductivity material including but not limited to copper and aluminum. The LED or LED arrays 16, 30, and 38 would be attached to LED printed circuit boards (PCBs) 18, 28, and 36 which would in turn be thermally and mechanically attached to heat sinks 12, 25, and 34 respectively. In a preferred embodiment the PCBs would be made out of a high thermal conductivity material including but not limited to copper, diamond, aluminum, or composite materials. Ideally the thermal resistance between the back side of the LED die or die arrays would be minimized by direct eutectic attachment, soldering, or thermally conductive epoxy. The high thermal conductivity PCBs would act as heat spreaders thereby reducing the heat flux into the heat sinks 12, 25, and 34. The heat sinks could be cooled by direct convection with air, conduction with various coolant fluids such as water, or radiation into the surrounding environment. Heat pipes of various constructions have also been found to work very effectively as heat sinks Heat pipes and diamond could also be used as the PCB material as they both are very effective heat spreaders with performance well above that of pure copper.

Figure 2:
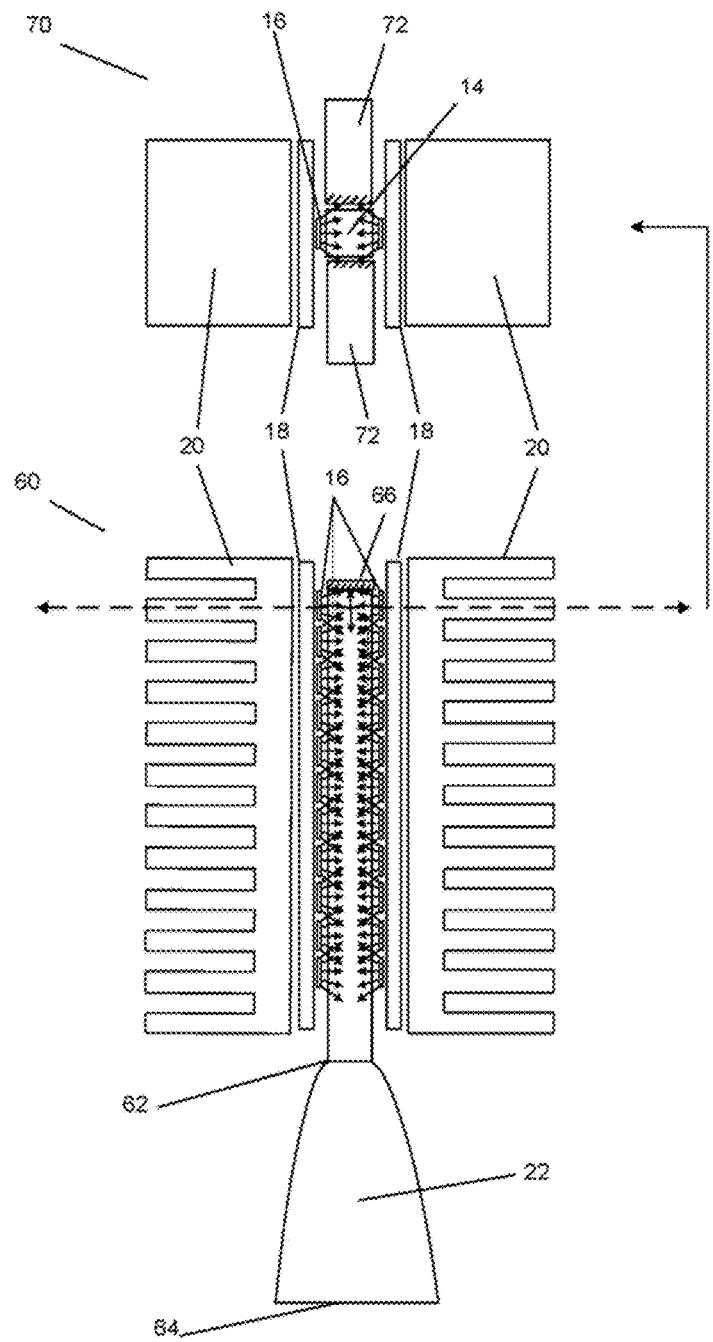
FIG. 2 is a detail of the solid rod luminescense material optical system comprised of the Ce:YAG rod, blue LED excitation sources, heat sinks, and index matched output optic. The top view represents a cross sectional view.

FIG. 2 shows a detailed view 60 of the LED module 12 of FIG. 1 from the side and in cross section as indicated in 70. The luminescent rod 14, which in a preferred embodiment would be single crystal or transparent sintered polycrystalline Ce:YAG would be characterized by high absorption in a spectral region such as blue in the region of 460 nm and very low extinction for wavelengths greater than the excitation wavelength band above 500 nm to 510 nm. The rod material 14 would also be characterized by exhibiting luminescence of the absorbed excitation light with high quantum yield. Thus the LED array 16 would in a preferred embodiment be comprised of blue LED die such as those manufactured by CREE Inc. called EZ1000 which are dimensionally on the order of 1 mm square by 0.120 mm thick. The light from the LED array would be transmitted through the outer wall of luminescent rod 14. The extinction coefficient of rod 14 would be doped to a level resulting in substantially all of the blue light being absorbed within the dimension of the rod prior to exiting the rod through its other side. To the extent that the excitation light was not absorbed with the first pass through the rod 14, mirrors 72 could be positioned with a reflective surface close to the rod so as to cause the excitation light to pass back into the rod one or more times to maximize absorption by the rod. The reflectivity of the LED die is on the order of 80% which would also act to couple light that was not absorbed on the first pass through the rod back into it for another opportunity to be absorbed. The light could take multiple passes to be substantially absorbed. Given the finite reflectivity of the mirrors 72 and diffuse reflectivity of the LED die 16 it would be best to chose an extinction that would result in the order of 80% or more of the excitation light being absorbed on the first pass through the rod 14. Alternatively, the sides of the rod through which the excitation light is not passing initially could be coated with a high reflectivity coating. It would be critical, however, that the reflectivity be very close to 100% so as not to loose substantial luminous power upon multiple reflections as the luminescent light is transmitted toward the output aperture 62. In a preferred embodiment the outside surface of the rod would not be coated at all so as to allow a substantial portion of the light generated within the rod to be guided by total internal reflection (TIR) up the rod toward output aperture 62. The fact that the luminescent material 14 has a relatively high index of refraction is fortunate as the higher the index of refraction the greater percentage of the light that is generated within the rod will be guided by TIR toward the output aperture 62.

The luminescent light generated within the rod 14 would be substantially isotropic and thus would travel equally in all directions. Thus half of the light that is bound to the rod by TIR would travel in a direction opposite to the output aperture 62 toward mirror 66 which would act to send the light emitted in that direction back toward output aperture 62, thereby substantially doubling the light reaching output aperture 62. The mirror could also be effectively coated directly onto the end face of rod 14 in the vicinity of mirror 66.

Figure 3:
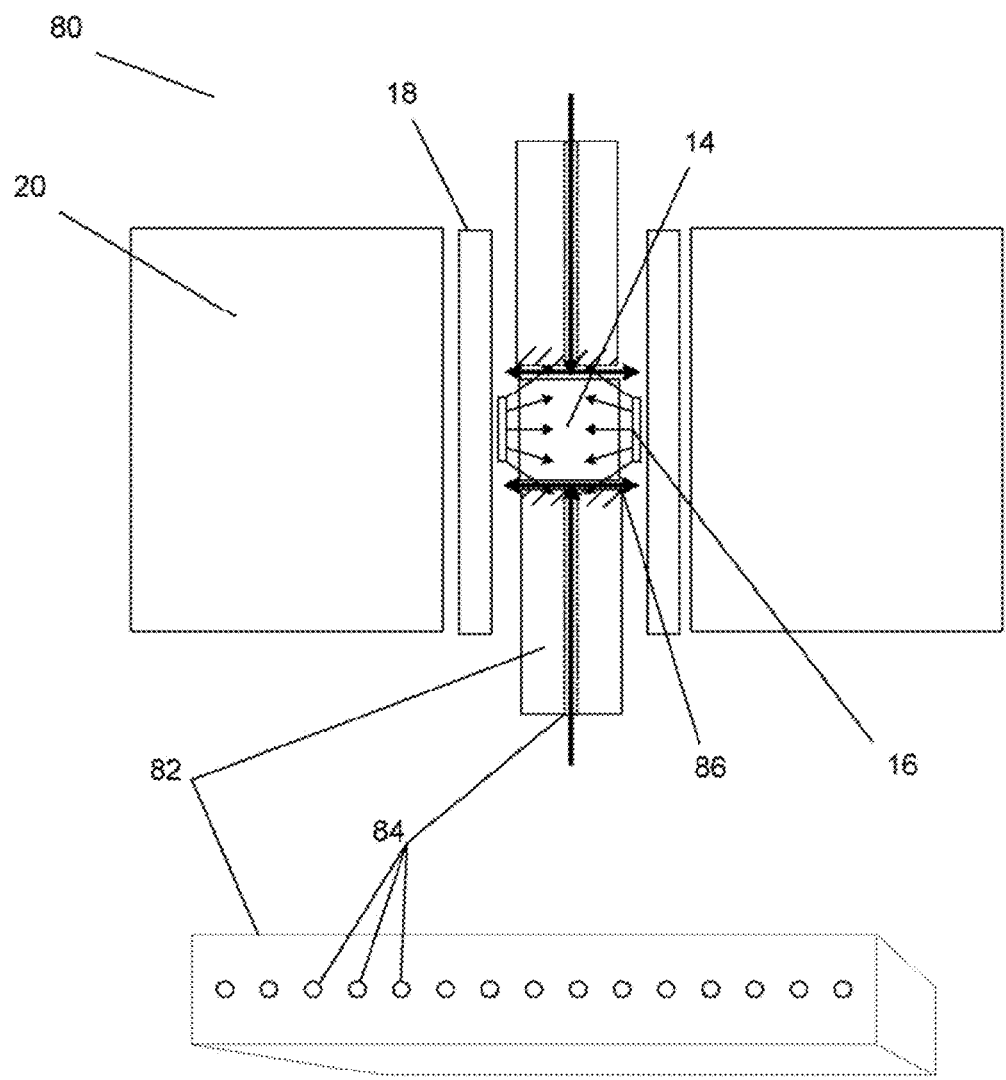
FIG. 3 is a preferred embodiment of the combined mirror and Ce:YAG cooling system.

FIG. 3 shows an alternative embodiment 80 of the mirror elements 66 of FIG. 2 comprised of modified mirror elements 82 containing the addition of small holes 84 through which high pressure air would cool rod 14 by high pressure air impingement. The holes would be sufficiently small as to minimally affect the mirrored surface area of mirrors 82. High pressure air impingement has several times the film coefficient and thus heat transfer as compared to standard convected low pressure air. The effect of the slight increase in the index of refraction of the medium surrounding rod 14 on TIR would be minimal. If direct contact cooling fluid was used without the sides of the rod being reflective, the higher than air index of refraction of the fluid would result in more loss out through the sides due to the decreased TIR internal angle, thereby reducing overall LED module efficiency. The reason it may be important to provide a means of removing heat build up from the rod is that there would be a small but finite heat absorption, convection and conduction to the rod from the LED array 16 that would cause an increase in temperature of the rod if there were no means of removing this heat. This heat rise would result in reduced LED module performance due to thermal quenching of the luminescent rod material. Increasing the temperature of the rod material can decrease the quantum efficiency.

Figure 4:
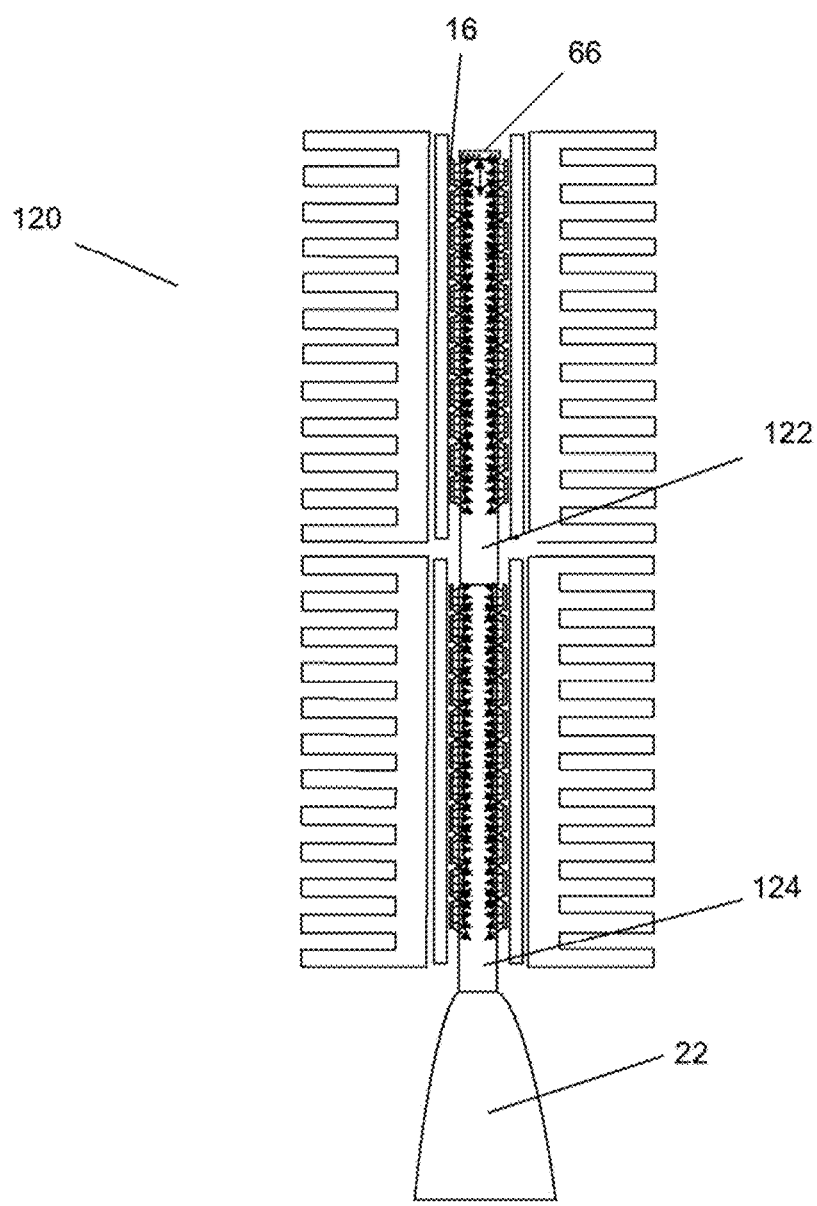
FIG. 4 shows an alternative embodiment containing two luminescent rod sources in series.

FIG. 4 shows an alternative embodiment 120 of LED module 12 of FIG. 1 where two modules 12 have been positioned in sequence to form a single multi-spectrum source. For example rod 122 of 120 could be made of a luminescent material with properties similar to those described for rod 14 for which the excitation band is within the long wavelength ultraviolet spectrum in the region of 240 nm to 420 nm. The high transmission region of the material would be in wavelengths longer than 420 nm and its luminescence could be in the blue to blue-green spectral region. Likewise rod 124 could have similar absorption properties but comprise luminescence in the green to red region of the spectrum. Both rods 122 and 124 would be characterized by high transmission in the spectral region containing wavelengths longer that 420 nm.

The mirror 66 would act to reflect any light transmitted in the direction opposite output coupler 22 back toward 22. In this way, LED light module 120 could contain the full and desired spectrum of the white light source and would not require supplemental LED modules 24 and 26 of FIG. 1 nor dichroic beam splitters 42 and 44. It would be necessary to use an index matching material between the two rods 122 and 124 such as melted Schott SF6 glass or other suitable index matching material. Alternatively, a single material or ceramic such as YAG (yttrium aluminum garnet) could use different dopants in the regions corresponding to rods 122 and 124 such that the rod is continuous and there is no need for an index matching medium. Alternatively, more than one dopant could be used evenly over the entire length of a single rod assuming the dopants did not interfere and reduce quantum efficiency. The length of the rods and excitation LED arrays could be increased to achieve higher flux out of collection optic 22. This is the primary distinction and advantage of this technology over prior art comprised of a thin planar luminescent material, as the out put can be increased by increasing the length of the rod rather than increasing the power density of the excitation source thereby resulting in output flux many multiples of that which could be achieved by prior art. The output of the system of FIG. 4 could alternatively be directly coupled to an optical fiber bundle without the need for re-imaging optics.

Figure 5:
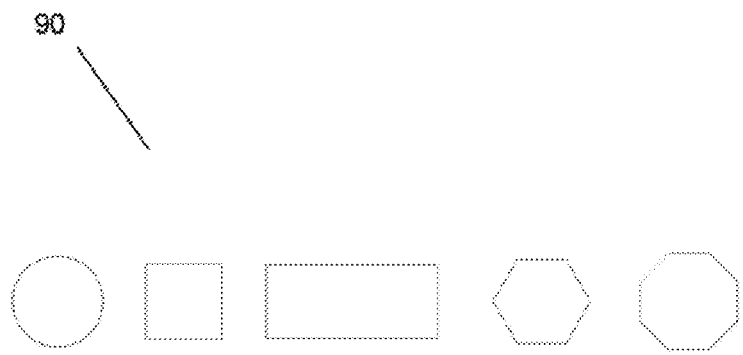
FIG. 5 shows various alternative cross sectional shapes.

FIG. 5 represents alternative cross sectional areas for rods including but not limited to circular, square, rectangular, and multiple sided polygons such as a hexagon and octagon. Generally, even number of sides polygons have better spatial mixing than those with an odd number of sides although either could be used. Likewise, the optical concentrator that would be index matched to one of the rod configurations could have a similar cross sectional shape. For example a rectangular or square CPC or taper could be used. A theta by theta CPC comprised of a taper coupled to a CPC such as described by Welford and Winston (High Collection Nonimaging Optics, W. T. Welford and R. Winston, Academic Press, 1989) could be used.

Figure 6:
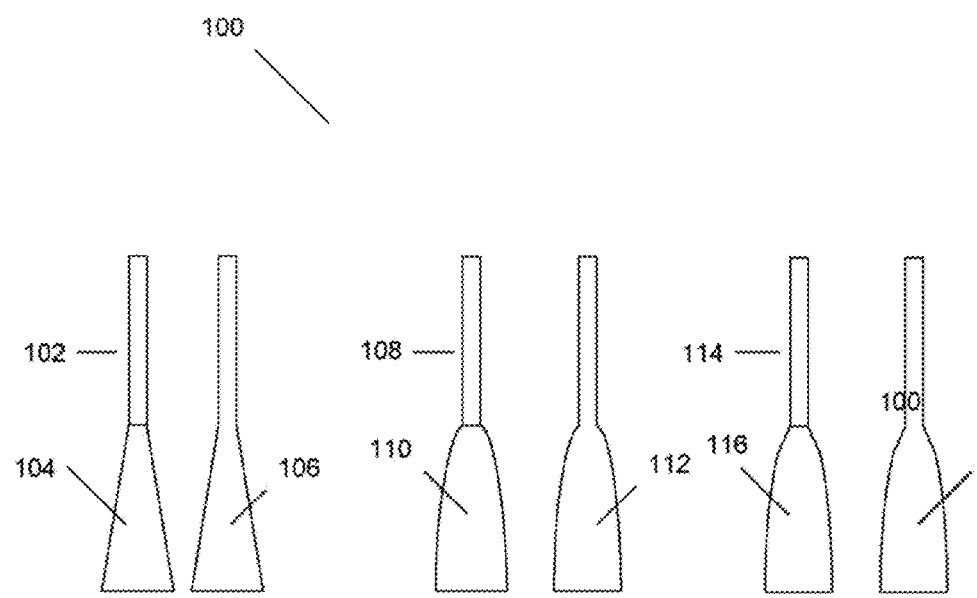
FIG. 6 shows three different output coupling optics attached to the luminescent material rod and also integrated as part of the rod.

FIG. 6 shows various configurations 100 of a combination of luminescent rod and output concentrators. For example the rods 102, 108, and 114, could be index matched to output couplers in the form of a taper 104, CPC 110, or combined theta by theta taper and CPC 116. In general the concentrators would be made out of a material that is transparent and of similar index of refraction and would be coupled by means of an index matching medium. Alternatively, the two components comprising a rod and concentrator could be mated by heating the components and allowing them to melt together. Alternatively, the rod and concentrator could be made out of the same material such as ceramic (phosphor particles sintered at temperatures on the order of 1800° Celsius and under pressure causing the material to become transparent and substantially homogeneous) such as Ce:YAG which could be doped in the region of the rod and not doped in the region of the concentrator thereby eliminating the need for index matching.

Figure 7:
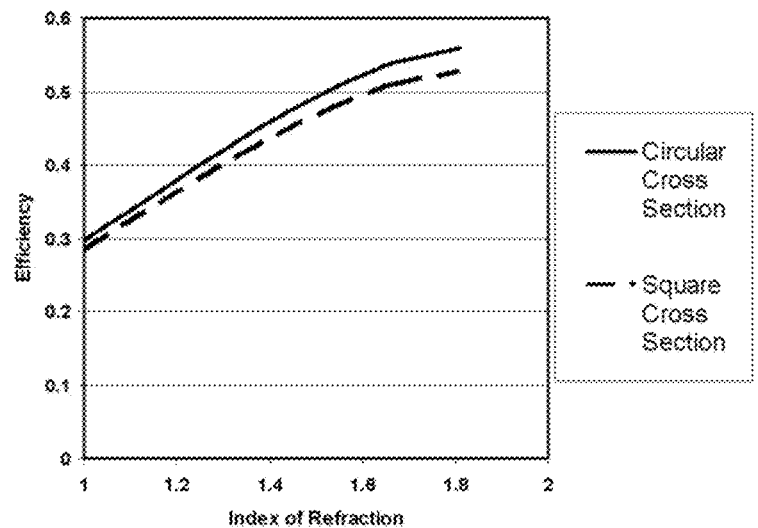
FIG. 7 shows a plot of efficiency of coupling light out of the end of the rod assuming different cross sectional shapes (___ circular vs - - - square) as a function of the index of refraction of the attached optic.

FIG. 7 shows a plot of index of refraction of the concentrator versus coupling efficiency for the case of Ce:YAG rod which has an index of refraction on the order of 1.82 for two rod geometries circular and square in cross section. The outcoupling efficiency into air (index of refraction 1) of 30% assumes that all the light emitted by the LED die is absorbed within the rod and that one end of the rod is coated with a mirror with reflectivity of 100%. Thus, the efficiency can be improved by the order of 80% by index matching to a concentrator with an index of refraction approaching that of the rod. The data also assumes that the output face of the concentrator is anti-reflection coated to minimize losses due to Fresnel reflections at the air/dielectric interface.

Figure 8:
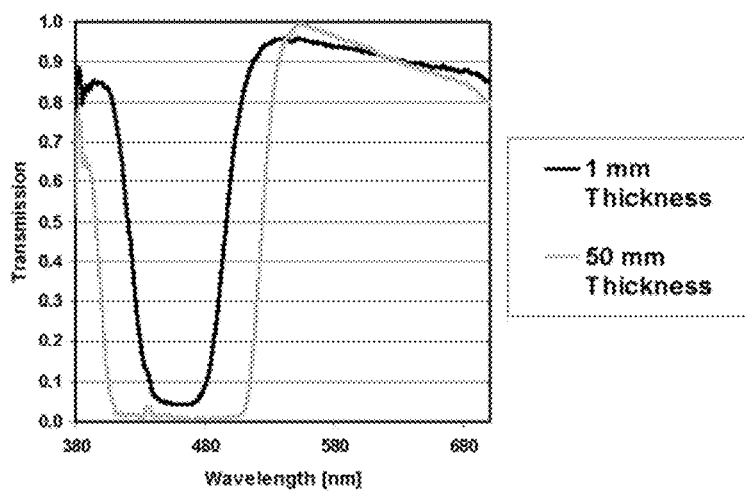
FIG. 8 shows the transmission spectrum of a white light source as a function of wavelength for two thicknesses (1 mm and 50 mm) for a 0.15% doped Ce:YAG rod.

FIG. 8 shows empirical data for a white light source transmitted through the side of a Ce:YAG rod of 1 mm in thickness as well as guided down its length of 50 mm. The Cerium doping was 0.15%. The data shows that for the 1 mm path length more than 90% of the blue light was absorbed. The rod was not coated, so the maximum expected transmission would be on the order of 84% due to Fresnel reflection which is observed at a wavelength of about 400 nm where the Ce:YAG rod is substantially transparent. The fact that the output is above the expected maximum transmission for wavelengths greater than 500 nm is due to the contribution from the luminescent light emitted by the absorbed blue light in the incident white light. The broader absorption band shown in the 50 mm length is due to the fact that Beer's Law is acting over 50 times the length exponentially. It is also apparent that the material does exhibit some degree of self absorption for which some of the absorbed light emitted as phosphorescence is absorbed through the length. Thus for some applications it may be important to limit the length of the rod to minimize absorption at the short end of the emitted spectrum and to minimize heating due to self absorption.

Figure 9:
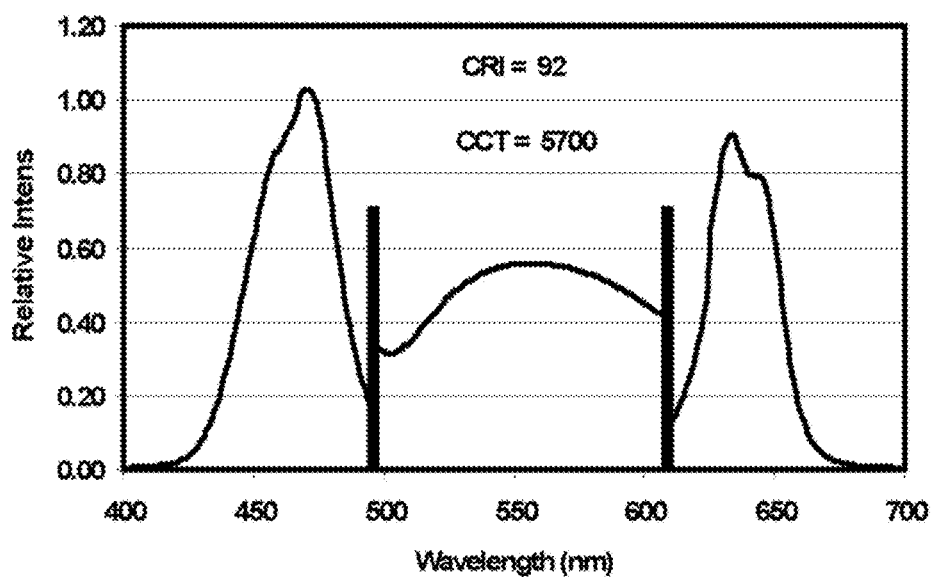
FIG. 9 shows a spectral plot of the relative intensity versus wavelength for three sources (blue, green and red) in the system of FIG. 1.

FIG. 9 shows the combined spectrum of the system of FIG. 1 with the thick black vertical lines representing the spectral region of the dichroic beam splitters. The current to the individual sources can be adjusted to result in a CRI greater than 90 at a CCT on the order of 5700° Kelvin which is consistent with the values typical of short arc Xenon lamps. The blue spectrum shown here is comprised of three blue LED peak wavelength centered around 445 nm, 457 nm and 470 nm. The red band is comprised of the combination of LED center wavelengths peaked near 630 nm and 650 nm. The effect of increasing the spectral widths in the blue and red spectral regions is primarily to increase the CRI.

The breadth and scope of the present invention should not be limited by any of the above-described exemplary embodiments, but should be defined only in accordance with the following claims and their equivalents.

What is claimed is:

1. A light engine for generating white light for endoscopy or microscopy, the light engine comprising:
    a first light source, wherein the first light source includes a plurality of first Light Emitting Diodes (LEDs) and a first concentrator, wherein the first light source emits a first light beam of a first color;
    wherein said plurality of first Light Emitting Diodes (LEDs) of said first light source emit light of an excitation color different than said first color, and wherein said first light source further comprises a luminescent rod comprising a luminescent material which absorbs said light of said excitation color and, in response, emits light of said first color which passes through said first concentrator to generate said first light beam of said first color;
    a second light source, wherein the second light source includes a second Light Emitting Diode (LED) and a second concentrator, wherein the second light source emits a second light beam of a second color different than the first color;
    a third light source, wherein the third light source includes a third Light Emitting Diode (LED) and a third concentrator, wherein the third light source emits a third light beam of a third color different than the first color and second color;
    a plurality of reflective optical components positioned so as to combine the first light beam of the first color, the second light beam of the second color, the third light beam of the third color, on a main optical axis of the light engine to generate a beam of white light; and
    an output system including one or more lens for focusing the beam of white light into a light guide for transmission to a microscope or endoscope.

2. The light engine of claim 1, wherein the light engine has the ability to control correlated color temperature (CCT) of the beam of white light.

3. The light engine of claim 1, wherein the light engine has the ability to control the color rendering index (CRI) of the beam of white light.

4. The light engine of claim 1, wherein the beam of white light has a color rendering index (CRI) of at least 85.

5. The light engine of claim 1, wherein the light engine has the ability to modulate the light output in synchronization with a camera shutter.

6. The light engine of claim 1, in combination with a light guide positioned to receive said beam of white light from said lens, wherein the light guide is adapted to transport said beam of white light to said microscope or endoscope.

7. The light engine of claim 1, wherein said plurality of reflective elements comprise a plurality of dichroic reflective elements.

8. The light engine of claim 1, wherein air is directed at a surface of the luminescent rod in order to cool the luminescent rod.

9. The light engine of claim 1, wherein the luminescent rod comprises one of a single crystal Ce:YAG and a sintered ceramic Ce:YAG.

10. The light engine of claim 1 wherein the output system further comprises a lens stop to prevent color fringe effects.

11. The light engine of claim 1, wherein the first color is green, the second color is blue, the third color is red, and the excitation color is blue.

12. A light engine for generating white light for an optical instrument, the light engine comprising:
    a first light source, wherein the first light source includes a plurality of first Light Emitting Diodes (LEDs) and a first concentrator, wherein the first light source emits a first light beam of a first color;
    wherein said plurality of first Light Emitting Diodes (LEDs) of said first light source emit light of an excitation color different than said first color, and wherein said first light source further comprises a luminescent rod comprising a luminescent material which absorbs said light of said excitation color and, in response, emits light of said first color which passes through said first concentrator to generate said first light beam of said first color;
    a second light source, wherein the second light source includes a second Light Emitting Diode (LED) and a second concentrator, wherein the second light source emits a second light beam of a second color different than the first color;
    a third light source, wherein the third light source includes a third Light Emitting Diode (LED) and a third concentrator, wherein the third light source emits a third light beam of a third color different than the first color and second color;
    a plurality of reflective optical components positioned so as to combine the first light beam of the first color, the second light beam of the second color, the third light beam of the third color, on a main optical axis of the light engine to generate a beam of white light; and
    an output system including one or more lens for focusing the beam of white light into a light guide for transmission to said optical instrument.

13. The light engine of claim 12, wherein the beam of white light has a color rendering index (CRI) of at least 85.

14. The light engine of claim 13, wherein said plurality of reflective elements comprise a plurality of dichroic reflective elements.

15. The light engine of claim 13, wherein the luminescent rod comprises one of a single crystal Ce:YAG and a sintered ceramic Ce:YAG.

16. The light engine of claim 13, wherein the light engine has the ability to modulate the light output in synchronization with a camera shutter.

17. The light engine of claim 13, wherein air is directed at a surface of the luminescent rod in order to cool the luminescent rod.

18. The light engine of claim 12, wherein the light engine has the ability to control correlated color temperature (CCT) of the beam of white light.

19. The light engine of claim 12, wherein the light engine has the ability to control the color rendering index (CRI) of the beam of white light.

20. A light engine for generating white light for endoscopy or microscopy, the light engine comprising:
a first light source, wherein the first light source includes a plurality of first Light Emitting Diodes (LEDs) and a first concentrator, wherein the first light source emits a first light beam of a first color;
wherein said plurality of first Light Emitting Diodes (LEDs) of said first light source emit light of an excitation color different than said first color, and wherein said first light source further comprises a luminescent rod comprising a luminescent material which absorbs said light of said excitation color and, in response, emits light of said first color which passes through said first concentrator to generate said first light beam of said first color;
a second light source, wherein the second light source includes a second Light Emitting Diode (LED) and a second concentrator, wherein the second light source emits a second light beam of a second color different than the first color;
a third light source, wherein the third light source includes a third Light Emitting Diode (LED) and a third concentrator, wherein the third light source emits a third light beam of a third color different than the first color and second color;
a plurality of reflective optical components positioned so as to combine the first light beam of the first color, the second light beam of the second color, the third light beam of the third color, on a main optical axis of the light engine to generate a beam of white light;
a light guide adapted to couple the light engine to an endoscope or microscope, and
an output system including one or more lens for focusing the beam of white light into said light guide for transmission to said endoscope or microscope.

21. The light engine of claim 20, wherein the beam of white light has a color rendering index (CRI) of at least 85.

22. The light engine of claim 20, wherein said plurality of reflective elements comprise a plurality of dichroic reflective elements.

23. The light engine of claim 20, wherein the luminescent rod comprises one of a single crystal Ce:YAG and a sintered ceramic Ce:YAG.

24. The light engine of claim 20, wherein the light engine has the ability to modulate the light output in synchronization with a camera shutter.

25. The light engine of claim 20, wherein the light engine has the ability to control correlated color temperature (CCT) of the beam of white light.

26. The light engine of claim 20, wherein the light engine has the ability to control the color rendering index (CRI) of the beam of white light.

27. The light engine of claim 13, in combination with a light guide positioned to receive said beam of white light from said lens, wherein the light guide is adapted to transport said beam of white light to said microscope or endoscope.

* * * * *